US00PP31664P2

(12) United States Plant Patent
Bakale, Jr.

(10) Patent No.: US PP31,664 P2
(45) Date of Patent: Apr. 14, 2020

(54) ***SYRINGA* PLANT NAMED 'JDB123WHITEHOUSE'**

(50) Latin Name: *Syringa meyeri*
Varietal Denomination: JDB123WHITEHOUSE

(71) Applicant: John David Bakale, Jr., Allendale, MI (US)

(72) Inventor: John David Bakale, Jr., Allendale, MI (US)

( * ) Notice: Subject to any disclaimer, the term of this patent is extended or adjusted under 35 U.S.C. 154(b) by 0 days.

(21) Appl. No.: 16/350,709

(22) Filed: Dec. 27, 2018

(51) Int. Cl.
*A01H 5/02* (2018.01)
*A01H 6/00* (2018.01)

(52) U.S. Cl.
USPC ..... Plt./248
CPC ..... *A01H 6/00* (2018.05)

(58) Field of Classification Search
USPC ..... Plt./248
See application file for complete search history.

(56) References Cited

U.S. PATENT DOCUMENTS

PP24,252 P2 2/2014 Van Nijnatten

*Primary Examiner* — Anne Marie Grunberg
(74) *Attorney, Agent, or Firm* — Buchanan Ingersoll & Rooney PC

(57) ABSTRACT

A new and distinct variety of *Syringa meyeri Syringa* plant, herein referred to by its cultivar name, 'JDB123WHITEHOUSE', is provided which forms light pink to white colored flowers. Dark green colored foliage is formed. The new variety provides vegetation that is moderately vigorous and the growth habit is rounded. The new variety is well suited for providing attractive ornamentation in the landscape.

2 Drawing Sheets

Botanical/commercial classification:
Latin name—*Syringa meyeri.*
Common name—*Syringa* Plant.
Varietal denomination—'JDB123WHITEHOUSE'.

SUMMARY OF THE INVENTION

The new variety of *Syringa meyeri Syringa* plant was discovered in West Olive, Mich. and was created as the result of open-pollination. The female parent (i.e., the seed parent) was the 'Palabin' variety (not patented). The male parent (i.e., the pollen parent) was unknown.

The parentage of the new variety can be summarized as follows:

'Palabin' x unknown

The new cultivar was discovered and selected as a single flowering plant within the progeny of the progeny of the above stated open-pollination during May 2008 in a controlled environment in West Olive, Mich.

It was found that the new variety of *Syringa* plant of the present invention possesses the following combination of characteristics:

(a) forms attractive, light pink to white colored flowers,
(b) exhibits dark green-colored foliage,
(c) provides moderately vigorous vegetation, and
(d) displays rounded growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'Palabin' variety (i.e., the seed parent) displays pink colored flowers and exhibits an upright growth habit, whereas the new variety displays light pink to white colored flowers and exhibits a rounded growth habit. Moreover, the new variety can be readily be distinguished from related similar non-parental varieties. For example, the 'Pink Perfume' variety (U.S. Plant Pat. No. 24,252) has a darker pink colored flower compared to the new variety.

The new variety has been found to undergo asexual propagation at West Olive, Mich. by terminal stem cuttings since June 2011. Asexual propagation by terminal stem cuttings at West Olive, Mich. has shown that the characteristics of the new variety are stable and are strictly transmissible by such asexual propagation from one generation to another. Accordingly, the new variety undergoes asexual propagation in a true-to-type manner.

The new variety has been named 'JDB123WHITEHOUSE'.

BRIEF DESCRIPTION OF THE PHOTOGRAPHS

The accompanying photographs shows as nearly true as it is reasonably possible to make the same, in color illustrations of this character, typical specimens of the new variety. The *Syringa* plants of the new variety were grown in 3-gallon containers for three years growing in an outdoor nursery at West Olive, Mich. and in early April 2017 the plants were transported to Cochranville, Pa. and held under outdoor nursery conditions.

Figure 1:
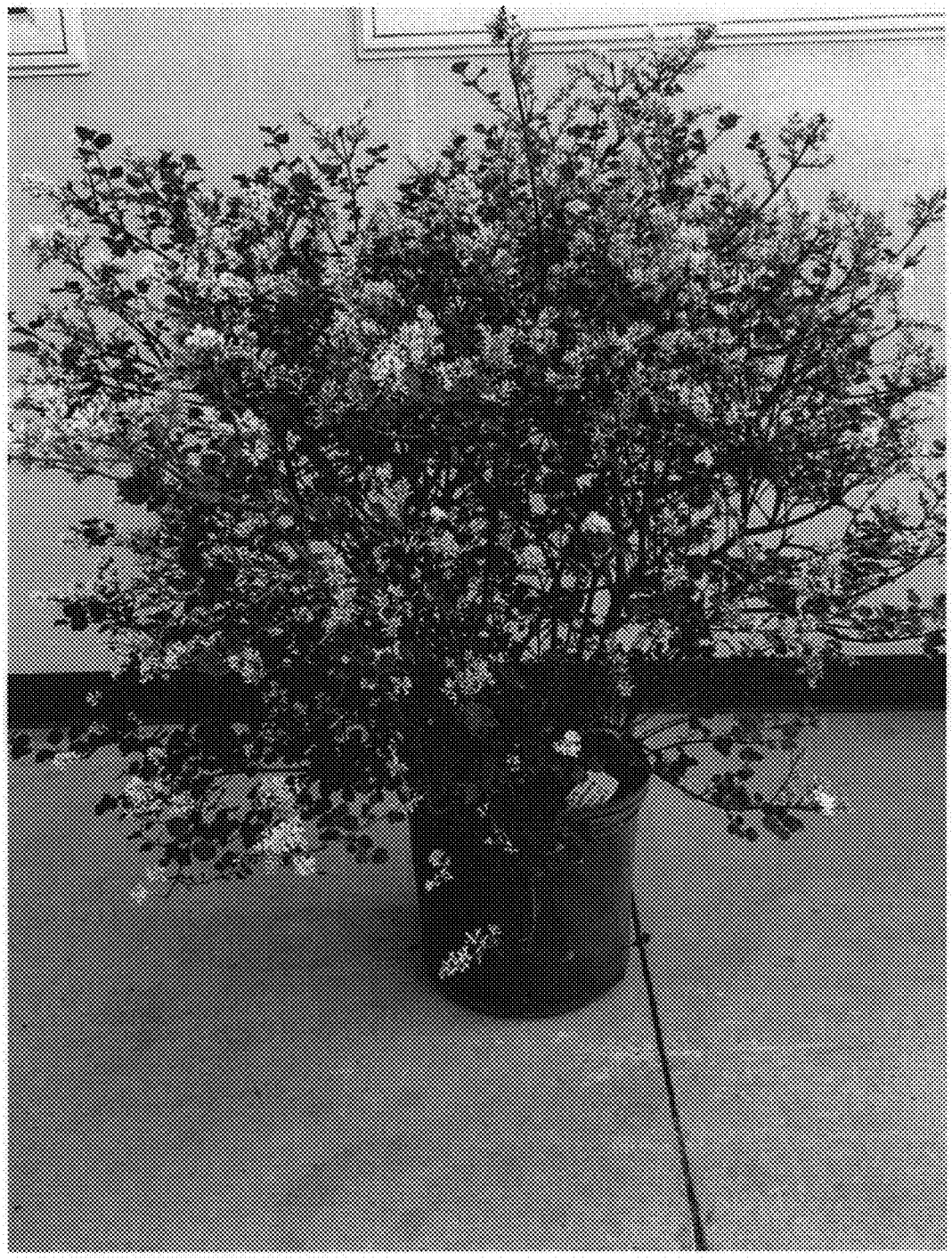

FIG. 1—illustrates a specimen the plant—side view—displaying the overall growth and flowering habit.

Figure 2:
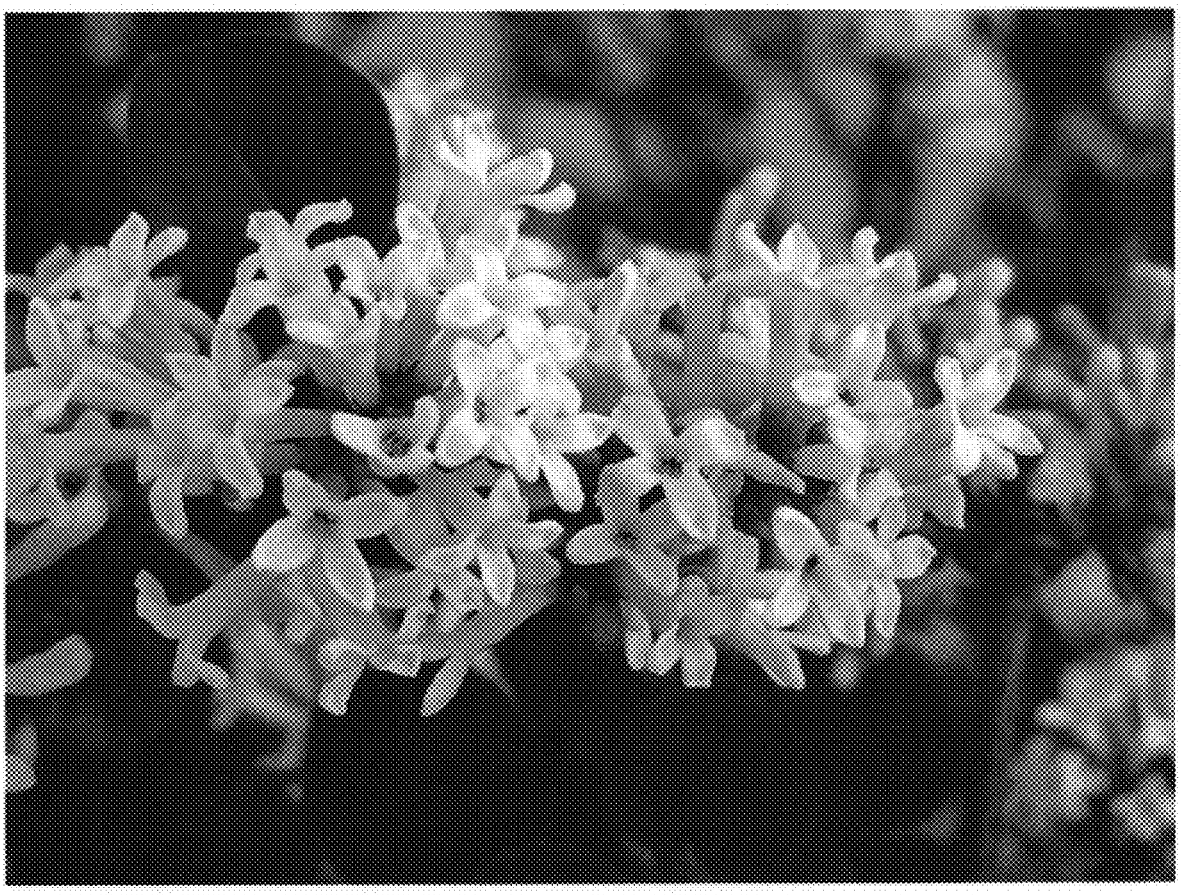

FIG. 2—illustrates a specimen of a flower—close view.

DETAILED BOTANICAL DESCRIPTION

The chart used in the identification of the colors is that of The Royal Horticultural Society (R.H.S. Color Chart, 2015

Edition), London, England, except where general color terms of ordinary significance are used. The terminology which precedes reference to the chart has been added to indicate the corresponding color in more common terms. The color values were determined in April 2019 under natural light conditions in Cochranville, Pa.

The following description and measurements is based on specimens of the new variety produced from cuttings from stock plants. The plants were grown in 3-gallon containers utilizing a soilless growth medium for three years in an outdoor nursery in West Olive, Mich. In April 2017, the plants were transferred to Cochranville, Pa. and held under outdoor nursery conditions to flower. Measurements and numerical values represent averages of typical plants.

Class: *Syringa* Plant.

Propagation:

*Type cutting*.—Terminal cuttings.

*Time to initiate roots*.—Approximately 3 weeks.

*Time to produce a rooted cutting*.—Approximately 12 weeks.

*Root description*.—Fibrous and fine; white to brown in color.

*Rooting habit*.—Freely branching; dense.

Plant:

*Growth habit*.—Rounded.

*Commercial crop time*.—Approximately 12 months from a rooted cutting to finish in a one-gallon container.

*General appearance*.—Shrub.

*Size*.—Height from soil level to top of plant plane: approximately 60.0 cm. Width: approximately 85.0 cm.

*Branching habit*.—Freely branching. Quantity of branches per plant: approximately 6 main stems per plant with approximately 5 to 7 lateral branches per stem.

*Lateral branches*.—Strength: strong. Length: approximately 19.0 cm long. Diameter: approximately 5.0 mm. Length of central internode: approximately 2.0 cm. Texture of mature stem: woody. Color of mature stems: commonly near Grey-Brown Group 199A.

Foliage:

*General description*.—Form: simple. Arrangement: alternate. Fragrance: none detected.

*Leaves*.—Aspect: 45° to stem. Shape: deltoid to orbicular. Margin: entire. Apex: rounded to obtuse. Base: rounded. Venation pattern: pinnate. Length of mature leaf: approximately 1.6 cm. Width of mature leaf: approximately 1.5 cm. Texture of upper and lower surfaces: glabrous. Color of upper surface of mature foliage: commonly near Green Group 138A. Color of lower surface of mature foliage: commonly near Green Group 138B.

*Petiole*.—Length: approximately 5.0 to 8.0 mm. Diameter: less than 1.0 mm. Texture: glabrous. Color of upper and lower surfaces: commonly near Green Group 138B.

Inflorescence:

*Flower arrangement and flowering habit*.—Single salverform flowers arranged and axillary terminal panicles; freely flowering habit with usually about 110 flowers per inflorescence; flowers face upright to slightly outwardly.

*Lastingness of individual inflorescence on the plant*.—Approximately 10 days, flowers not persistent.

*Fragrance*.—Strongly fragrant; fragrance sweet and pleasant.

*Inflorescence size*.—Height: about 5.0 cm. Diameter: about 4.0 cm.

*Flower size*.—Diameter: about 7.0 mm. Length (height): about 1.0 cm.

*Flower buds*.—Length: about 11.0 mm. Diameter: about 2.0 mm. Shape: spatulate. Color: commonly near Purple Group 76D.

*Petals*.—Quantity and arrangement: single whorl of four petals; lower 80% of petals fused forming a narrow tube. Lobe length: about 4.0 mm. Lobe width: about 2.0 mm. Lobe shape: narrowly oblanceolate. Apex: acute. Margin: entire. Texture of upper and lower surfaces: smooth, glabrous. Color when opening and fully opened, upper and under surfaces: commonly near Purple Group 76D. Color when fading, upper and under surfaces: commonly near White Group NN155C.

*Sepals*.—Quantity and arrangement: single whorl of four sepals; fused towards the base forming a campanulate-shaped calyx. Length: about 2.0 mm. Width: about 1.0 mm. Apex: acute. Margin: entire. Texture of upper and lower surfaces: pubescent. Color of upper and lower surfaces: commonly near Green Group 145A blending closer to Yellow-Green Group 145B towards the apex.

*Peduncles*.—Length: about 4.0 cm. Diameter: about 1.0 mm. Strength: strong. Texture: smooth, glabrous. Color: commonly near Grey-Brown Group 199A.

*Reproductive organs*.—Androecium: Stamen quantity: 2 per flower. Stamen length: approximately 3.0 mm. Anther shape: oblong. Anther length: approximately 3.0 mm. Anther color: commonly near Grey-Brown Group N199A. Pollen amount: moderate. Pollen color: commonly near Yellow Group 2D. Gynoecium: Pistil quantity: 1 per flower. Pistil length: approximately 2.0 mm. Stigma shape: club-shaped. Stigma length: less than 1.0 mm. Stigma color: commonly near Green-White Group 157D. Style length: approximately 1.5 mm. Style color: commonly near Green-White Group 157D. Ovary diameter: less than 1.0 mm. Ovary color: commonly near Green Group 143C.

*Seed and fruit production*.—Neither seed nor fruit production has been observed.

Development:

*Vegetation*.—Moderately vigorous.

*Flowering season*.—Plants of the new variety flower in early spring in Cochranville, Pa.

*Hardiness*.—USDA Zone 5.

*Disease and pest resistance*.—Resistance to pathogens and pests common to *Syringa* has not been observed.

The new 'JDB123WHITEHOUSE' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of *Syringa* plant characterized by the following combination of characteristics:

(a) forms attractive, light pink to white colored flowers, (b) exhibits dark green-colored foliage, (c) provides moderately vigorous vegetation, and (d) displays rounded growth habit;
substantially as herein shown and described.

* * * * *